United States Patent [19]

Bentz

[11] Patent Number: 4,859,647
[45] Date of Patent: Aug. 22, 1989

[54] CATALYST COMPOSITIONS AND COMPOSITIONS CATALYZED THEREWITH

[75] Inventor: Peter O. Bentz, Waterloo, Belgium

[73] Assignee: Dow Corning, Ltd., Barry, Wales

[21] Appl. No.: 21,366

[22] Filed: Mar. 3, 1987

[30] Foreign Application Priority Data

Mar. 18, 1986 [GB] United Kingdom ............... 8606634

[51] Int. Cl.$^4$ .................................... B01J 31/28
[52] U.S. Cl. ................................. 502/165; 502/158; 528/10
[58] Field of Search ............ 502/158, 165, 401, 345; 556/9, 401, 407, 415, 410; 528/10

[56] References Cited

U.S. PATENT DOCUMENTS

| | | | |
|---|---|---|---|
| 3,833,505 | 9/1974 | Brown | 556/410 |
| 4,122,118 | 10/1978 | George et al. | 502/165 |
| 4,220,556 | 9/1980 | Oswald et al. | 502/158 |
| 4,248,993 | 2/1981 | Takago | 556/415 |
| 4,257,916 | 3/1981 | Hancock et al. | 502/158 |
| 4,282,336 | 8/1981 | Yonezawa et al. | 556/410 |
| 4,283,505 | 8/1981 | Kleeberg et al. | 556/410 |
| 4,310,640 | 1/1982 | Kato et al. | 556/410 |
| 4,324,873 | 4/1982 | Wada et al. | 502/158 |
| 4,389,518 | 6/1983 | Harada et al. | 502/158 |
| 4,400,327 | 8/1983 | Baskent et al. | 502/158 |
| 4,689,422 | 8/1987 | Sawicki et al. | 502/558 |

FOREIGN PATENT DOCUMENTS

| | | | |
|---|---|---|---|
| 1016592 | 1/1966 | United Kingdom | 502/158 |
| 1203071 | 8/1970 | United Kingdom | 502/165 |

Primary Examiner—Anthony McFarlane
Attorney, Agent, or Firm—Roger H. Borrousch

[57] ABSTRACT

A composition comprising a complex of a Cu(II) salt formed from copper or a copper salt, an organosilicon compound having at least one Si-bonded group which include 2 amino nitrogens which may enter into a heterocyclic ring structure with Cu and 2 to 5 carbon atoms linking the N atoms, and water in the presence of oxygen, is useful as a catalyst for oxidative coupling reactions of certain silicon compounds. Formulations comprising up to 5 parts of the above composition and 100 parts of either arylolsilicon compounds or arylcyanophenylacetylsilicon compounds are particularly claimed.

22 Claims, No Drawings

CATALYST COMPOSITIONS AND COMPOSITIONS CATALYZED THEREWITH

This invention is concerned with catalyst compositions and compositions catalysed therewith and is particularly concerned with curing organosilicon compounds by an oxidative coupling reaction.

Organosiloxanes which may be cured via an oxidative coupling reaction include phenylcyanoacetyl-functional polysiloxanes and phenol-functional polysiloxanes for example those having a hydroxyphenylene or a (hydroxy phenyl)-alkylene group as disclosed in U.K. patent specification No. 1 203 071. In said specification there are disclosed compositions curable at room temperature to elastomers on exposure to atmospheric oxygen comprising an arylolsilicon compound chosen from certain arylolsilanes, arylolsiloxanes or copolymeric arylolsiloxanes and a basic copper salt complex with certain nitrogen containing heterocyclic compounds as exemplified by pyridine, said complex being soluble in the arylolsilicon compound. Whilst such compositions are attractive from various viewpoints, the catalysts are complexes which preferably are derived from pyridine which is a material not generally favoured due to physiologically harmful properties.

It is an object of the present invention to provide an improved catalyst material capable of accelerating an oxidative reaction between for example arylolsilicon or arylcyanoacetylsilicon compounds.

We have now found that a catalyst for an oxidative reaction between arylolsilicon or arylcyanoacetylsilicon compounds comprises a copper complex of certain diamino siloxane compounds.

The invention provides in one of its aspects a composition comprising a complex of a copper salt in oxidation state II formed by mixing in the presence of oxygen, water, copper or a copper salt, an organosilicon compound including at least one unit according to the general formula (i)

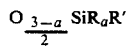

in which each R represents a monovalent group attached to the silicon atom, R' represents a group including two amino nitrogen atoms linked by a group R" having a structure such that the two nitrogen atoms enter into a heterocyclic ring structure including two nitrogen atoms, a copper atom and from 2 to 5 inclusive carbon atoms linking the nitrogen atoms and a is an integer with a value of less than 4.

A composition according to the invention contains a complex in which copper is present in oxidation state II. This appears to be essential in order to achieve the desired catalytic properties. The particular anion of the copper salt employed has no effect on the type of product obtained. Either a cupric or cuprous salt and also copper metal which is oxidized in situ to a cupric salt can be employed. The only requirement is that the salt must be capable of existing in the cupric state and must form a complex with the organosilicon compound which has solubility in the reaction medium employed for the oxidative reaction. Copper salts suitable for preparation of the complex include cuprous chloride, cupric chloride, cuprous bromide, cupric bromide, cuprous sulfate and cupric sulfate.

Organosilicon compounds suitable for use in forming the complex of the copper salt include at least one unit having a substituent including two amino nitrogen atoms. It is believed that unbonded pairs of electrons of the nitrogen atoms become associated with copper atoms in forming the complex, and that the group linking the two amino nitrogen atoms influences the stability of the complex and therefore its catalytic activity. The most suitable group R' for catalysis of oxidative cure of a particular composition depends to some extent on the nature of that composition. Thus, the group R' includes aromatic or cycloaliphatic or aliphatic groups. However, for oxidative cure of arylolsilicon or arylcyanoacetylsilicon compounds comprising arylol or arylcyanoacetyl polyorganosiloxanes to promote crosslinking thereof, we prefer to employ a diamino substituent R' according to the general formula (iii) $R^3N(Q)R''NQ_2$ in which $R^3$ represents an alkylene group having a chain of at least three carbon atoms linking silicon and nitrogen atoms, R" represents an alkylene group having from 2 to 5 inclusive carbon atoms linking the nitrogen atoms and each Q represents a hydrogen atom or an alkyl group attached to a nitrogen atom. Most preferably, R" is an ethylene group (whereby the heterocyclic ring system comprises two carbon atoms) each Q is a methyl or an ethyl group and $R^3$ is propylene.

The organosilicon compound used in preparing a composition according to the invention comprises one or more than one unit according to the formula (i). For example the unit (i) can take the form $R^3SiR'$ e.g. $(CH_3)_3Si(CH_2)_3N(CH_3)CH_2CH_2N(CH_3)_2$ or $RR'SiO$. It is necessary for these units (i) to diffuse in the composition to be catalysed and therefore the presence of no more than two or three units of formula (i) per organosilicon molecule is regarded as appropriate. Preferred organosilicon compounds are organosiloxanes in which a has the value 1 or 2, and which also include at least one unit according to the general formula (ii)

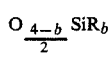

in which each R is as defined above and b has a value of 0, 1, 2 or 3. The units of (i) may be present as capping or crosslinking units, but preferably are present as chain units i.e. preferably a has the value 1. The units of the formula (ii) present in the organosiloxane promote solubility of the complex in polydiorganosiloxane media and insolubility in water. For many purposes it is desirable that the organosiloxane have many units of formula (ii), but increasing numbers of these units lead to polyorganosiloxanes which are less mobile within the formulation to be catalysed. Preferred compositions according to the invention comprise complexes which are soluble in the formulation to be catalysed. However, satisfactory oxidative curing may be achieved by use of complexes which are effectively in the form of substantially stable colloidal solutions which are readily miscible with the formulation to be catalysed for suitable dispersion therein. Thus, it may be desirable to include an organic liquid as solvent to produce such colloidal solution especially when using complexes which employ an organosiloxane having only a small number of units according to the general formula (ii). For many purposes organosiloxanes having from 2 to 50 units of formula (ii) are satisfactory. Preferably the organosiloxane is according to the average general formula (iii) $R_3Si(OSiR_2)_x(OSi(R)R^3N(Q)R''NQ_2)_yOSiR_3$ in which x has a value from 5 to 30, more preferably from 12 to 20 and y has a value from 1 to 3.

The substituents R in formulae (i) and (ii) are monovalent groups, and may be any of those groups conventionally present in polydiorganosiloxanes provided they do not interfere with preparation of the complex and do not adversely affect the performance of the complex in catalysing cure of formulations in which it is employed. The most suitable monovalent groups in this context are those compatible with those of the formulation to be catalysed. For many purposes the most appropriate monovalent groups are the lower alkyl groups for example methyl groups. For use with formulations to be catalysed which comprise polymers having significant quantities of dimethylsiloxane units, we prefer that at least 85% of the R substituents of the organosiloxane employed to provide the complex are methyl groups.

A composition according to the invention is formed from the copper salt, the organosilicon compound and water in presence of oxygen. The materials may be mixed together in any convenient order. If desired, a mutual solvent (for example methanol) may be included in the composition for example to enhance miscibility and/or solubility of the complex in the formulation to be catalysed. The composition may be formed in situ in the formulation to be catalysed, for example, by mixing the copper salt and organosilicon compound, adding this mixture and water to the formulation to be catalysed and bubbling oxygen through the formulation. Preferably, however, the composition comprising the complex is prepared prior to admixture with the formulation to be catalysed. For example one may mix an aqueous solution of the copper salt in the organosilicon compound. Stirring of the mixture in air, with or without bubbling air through the mixture, introduces sufficient oxygen for production of the complex.

A composition according to the invention may be employed to catalyse oxidative coupling reactions of formulations comprising polysiloxanes curable by an oxidative coupling reaction, for example, polysiloxanes having substituted phenol, phenylcyanoacetic acid ester and amide substituents. A composition according to the invention is soluble or at least colloidally soluble in polysiloxanes and insoluble in water. It is thus not readily leached from oxidatively cured polysiloxane formulations by water. It uses amino compounds which are less physiologically undesirable than pyridine compounds. By use of these compositions, it is possible to provide formulations comprising arylolsilicones or arylcyanoacetylsilicones which are fluid at room temperature and which remain workable in absence of oxygen and which crosslink on exposure to air or oxygen at room temperature via oxidative cure of, for example, phenolic or phenylcyanoacetyl groups linked to polysiloxane molecules and may thus find use for example in sealants, potting compounds or coatings.

Arylolsilicones which may be employed in such curable formulations include arylolsilicon compounds as defined. By the expression arylolsilicon compounds as defined is meant polysiloxanes comprising units according to the general formula (iv)

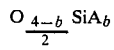

and at least one unit per polysiloxane chain according to the general formula (v)

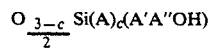

in which each A represents a monovalent hydrocarbon group, a halogenated monovalent hydrocarbon group, a cyanoalkyl group or an unsaturated hydrocarbon group attached to the silicon atom, each A' represents a substituted or unsubstituted divalent group and A'' represents a phenylene radical or a substituted phenylene radical, b has the value 0, 1, 2 or 3 ad c has the value 0, 1, 2 or 3.

Conveniently, the preferred polysiloxanes comprise units in which R and A are alkyl groups or phenyl groups, the most preferred groups for R and A being methyl groups.

The group A' may be any suitable chain linking the A''OH groups to the silicon atom. It may have substituents in the chain for example oxygen or on the chain, for example, halogen. We prefer to employ an alkylene group, for example, a propylene group.

The group A'' is preferably a substituted phenylene group in which the substituent is a lower alkyl or alkoxy group, for example, a methyl, ethyl, propyl, butyl or methoxy group. We believe that formulations containing the preferred arylolsilicon compounds in which a preferred composition according to the invention is included as catalyst material, cures in presence of oxygen via carbon-carbon coupling between phenyl groups to yield diphenoquinone linkages and/or via carbon-oxygen coupling between phenolic hydroxyl groups and phenyl groups to yield phenyl ethers or polyphenylene ethers. The mechanism involved is dependent on the substituent group on the phenol, which may bias the reaction, for example due to steric hindrance or electronic influences. We believe that in the case of the preferred arylol silicon compounds, the curing reaction yields primarily linkages of the diphenoquinone type which serve as cross links between siloxane chains. Accordingly, the density of crosslinks produced is dependent upon the number of units according to formula (v) present per molecule. Useful products have been demonstrated which employ from about 2% to about 10% units of formula (v), per polydimethylsiloxane molecule.

A curable formulation may be provided by mixing an arylolsilicon compound and a composition according to the invention under inert conditions, for example in a nitrogen atmosphere. Other compounding ingredients may be included in such a formulation, for example fillers and extenders. Upon exposure to oxygen or air the formulations cure readily at room temperature to provide crosslinked products.

As soon as the formulation is exposed to air, the oxidative coupling starts as evidenced by the appearance of a brown colouration at the surface which gradually spreads away from the surface as the crosslinking proceeds. It is believed that the brown colouration is due to diphenoquinone linkages which are highly conjugated and show therefore an intensive light absorption. The rate at which curing occurs is dependent upon the concentration of complex employed and upon the nature of the groups A''OH.

In general, amounts up to 5% complex by weight of the formulation may be used, depending on whether short tackfree times or significant depth of cure are required. Generally, the skinover time and the tack-free time decrease as the concentration of the complex is increased. Selected formulations comprising a polysiloxane having about 95 units of dimethylsiloxane and 5 units of methylsiloxane units having 3-(2 hydroxy-3 methyl phenyl) propyl substituents per polysiloxane molecule, and 3% by weight of the formulation of a preferred complex, have skinover times of around 10–20 seconds and are tack-free within 10 minutes. Similar formulations containing 1% of complex achieve the same conditions in 2 and 20 minutes respectively. Similar formulations containing 0.1% complex formed no skin until after several hours, but the region under the surface down to a depth of 15 mm became slowly brown and within 24 hours the surface was tack-free. Thus, samples with higher amounts of complex cure more rapidly on the surface but cure more slowly as the reaction frontier moves away from the surface whereas samples with lower amounts of complex cure more slowly but more evenly in some depth.

If the complex concentration is higher than approximately 0.5% by weight of the formulation, a colloidal red precipitate may be formed in the uncured parts of the formulation and also in samples which are stored in absence of oxygen, for example under nitrogen. This colloidal red precipitate may be caused to dissolve again and so to disappear if the formulation is stirred and simultaneously exposed to air for some time. The formation of this red precipitate is thus reversible and does not appear to strongly influence the catalytic activity. When uncured samples of the selected formulations in which such a red precipitate had been formed were exposed to air, they started to cure immediately and formed a skin within minutes. The tack-free times were also comparable with those of freshly prepared formulations.

The rate of cure achieved at the surface and in depth, and the formation of red precipitate as aforesaid is dependent not only on the concentration of complex but also on the nature and number of crosslinking sites e.g. phenol groups available in the formulation to be cured. Formulations having less active sites, or lower concentration of sites, tend to exhibit greater depth of cure and slower surface cure for a given concentration of complex, and a reduced tendency to produce a red precipitate.

The invention provides in another of its aspects a composition comprising 100 parts by weight of an arylolsilicon compound comprising units according to the general formula (iv)

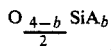

and at least one unit according to the general formula (iv)

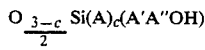

in which each A is selected from the group consisting of a monovalent hydrocarbon group, a halogenated monovalent hydrocarbon group, a cyanoalkyl group and an unsaturated hydrocarbon group attached to a silicon atom, each A' is selected from the group consisting of a substituted and an unsubstituted divalent group and A" is selected from the group consisting of a phenylene group and a substituted phenylene group, b and c are integers having a value of from 0 to 3.

Arylcyanoacetylsilicones which may be employed in compositions curable in the presence of a catalyst composition according to the invention include arylcyanoacetylsilicon compounds as defined. By the expression arylcyanoacetylsilicon compounds as defined is meant polysiloxanes comprising units according to the general formula (iv)

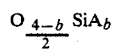

and at least one unit per polysiloxane chain according to the general formula (vi)

in which each A represents a monovalent hydrocarbon group, a halogenated monovalent hydrocarbon group, a cyanoalkyl group or an unsaturated hydrocarbon group attached to the silicon atom, each A' represents a substituted or unsubstituted divalent group, X represents an oxygen atom or the group =NH and Z represents a phenyl radical or a substituted phenyl radical, b has the value 0, 1, 2 or 3 and c has the value 0, 1, 2 or 3.

Conveniently, the preferred polysiloxanes comprise units in which A is an alkyl group or phenyl, the most preferred A being methyl groups.

The group A' may be any suitable chain linking the XC(O)CH(Z)(CN) groups to the silicon atom. It may have substituents in the chain, for example, oxygen or on the chain, for example, halogen. We prefer to employ an alkylene group, for example, a propylene group or an isobutylene group.

The group Z is preferably an unsubstituted phenyl group. Arylcyanoacetylsilicones can be either arylcyanoacetoxyalkyl or arylcyanoacetamidoalkyl silicones. The preferred arylcyanoacetylsilicones are those silicones having at least one silicon-bonded substituent of the formula

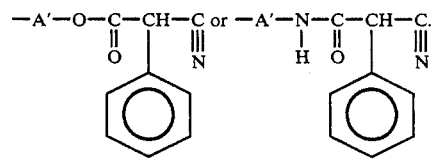

We believe that formulations containing the preferred arylcyanoacetylsilicon compounds in which a preferred composition according to the invention is included as catalyst material, cure in the presence of oxygen via carbon-carbon coupling between the CH groups to which the phenyl groups are linked. The curing reaction yields linkages which serve as cross links between siloxane chains. Accordingly, the density of crosslinks produced is dependent upon the number of units according to formula (vi) present per molecule. Useful products have been demonstrated which employ from about 2% to about 10% units of formula (vi), per polydimethylsiloxane molecule.

A curable formulation may be provided by mixing an arylcyanoacetylsilicon compound and a composition according to the invention under inert conditions, for example in a nitrogen atmosphere. Other compounding ingredients may be included in such a formulation, for example fillers and extenders. Upon exposure to oxygen e.g. oxygen of the air, the formulations cure readily at room temperature to provide crosslinked products.

As soon as the formulation is exposed to air, the oxidative coupling starts as evidenced by the formation of a skin on the surface. The rate at which curing occurs is dependent upon the concentration of complex employed.

In general, amounts up to 5% complex by weight of the formulation may be used, depending on whether short tackfree times or significant depth of cure are required. Generally the skinover time and the tack-free time decrease as the concentration of the complex is increased. Selected formulations comprising a polysiloxane having about 95 units of dimethylsiloxane and 5 units of methylsiloxane units having phenylcyanoacetamidopropyl substituents per polysiloxane molecule, and 1% by weight of the formulation of a preferred complex, have skinover times of around 30 minutes and are tack-free within 20 hours.

The invention provides in another of its aspects a formulation comprising 100 parts by weight of an arylcyanoacetylsilicon compound comprising units according to the general formula (iv)

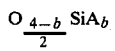

and at least one unit according to the general formula (vi)

in which each A is selected from the group consisting of a monovalent hydrocarbon group' a halogenated monovalent hydrocarbon group, a cyanoalkyl group and an unsaturated hydrocarbon group attached to a silicon atom, each A' is selected from the group consisting of a substituted and an unsubstituted divalent group, X is selected from the group consisting of an oxygen atom and the group =NH and Z is selected from the group consisting of a phenyl group and a substituted phenyl group, b and c have a value from 0 to 3.

There now follows a detailed description of three example compositions according to the invention and illustrative thereof, and of their use in oxidatively cured formulations. Me denotes a methyl group and Ph a phenyl group. It is to be understood that these compositions and formulations have been selected for description to illustrate the invention by way of example only and not by way of limitation thereof.

A first illustrative complex, which may be represented by the formula [Cu(OH)((Me$_3$SiO)$_2$MeSi(CH$_2$)$_3$N(CH$_3$)CH$_2$CH$_2$N(CH$_3$)$_2$)]$^+$$_2$Cl$^-$$_2$ was prepared by way of the reaction Cu$_2$Cl$_2$+(Me$_3$SiO)$_2$MeSi(CH$_2$)$_3$N(CH$_3$)CH$_2$CH$_2$N(CH$_3$)$_2$+H$_2$O+½O$_2$→ complex in the following way. 15.0 g (50 mmol) of (Me$_3$SiO)$_2$MeSi(CH$_2$)$_3$Cl and 19 ml (15 g) of N,N,N'-trimethylethylenediamine was heated to reflux ( 150° C.) for 4 hours with intensive stirring (separation into two phases). The mixture was cooled to room temperature with stirring until precipitation of crystals was completed. 25 ml ether was added to the mixture and the mixture filtered.

From the filtrate, the ether was distilled off and another 4 ml (3 g) of N,N,N'-trimethylethylenediamine was added and the mixture again heated up to reflux for 6 hours (again separation into two phases). After cooling the mixture, 25 ml ether was added and this mixture was kept overnight in a refrigerator. The solid was removed by filtration. From the filtrate, the ether was distilled off in vacuum at room temperature and the remaining yellow liquid was distilled in vacuum using a 20 cm Vigreux column. After a forecut of 2.0 g (bp$_{0.05}$ 50°–80° C.) the main fraction distilled at bp$_{0.05}$ of 80°–100° C. A yield of 14.0–15.0 g of (Me$_3$SiO)$_2$MeSi(CH$_2$)$_3$N(CH$_3$)CH$_2$CH$_2$N(CH$_3$)$_2$ was obtained.

0.99 g Cu$_2$Cl$_2$ was suspended in 3.0 ml methanol, 0.01 ml H$_2$O added and finally 3.65 g of (Me$_3$SiO)$_2$MeSi(CH$_2$)$_3$N(CH$_3$)CH$_2$CH$_2$N(CH$_3$)$_2$. The colour of the mixture changed from pale green to dark blue and after 15 hours stirring in an open flask to green-blue. After 15 hours all volatile compounds were distilled off in vacuum (bp$_{0.2}$ 40° C.). The remaining dark green oil partially solidified at room temperature. This oil was dissolved in 15 ml ether and filtered through diatomaceous silica to remove unreacted Cu$_2$Cl$_2$. From the filtrate, the ether was removed in vacuum (10 mbar/50° C.).

The dark green partly solidified oil was insoluble in water and petroleum ether, but soluble in toluene and acetone. It had poor solubility in polydimethylsiloxane fluid. However, a solution of the complex in toluene when mixed with polydimethylsiloxane gave a stable colloidal solution.

A second illustrative complex which may be represented by the formula [Cu(OH)(Me$_3$SiO(Me$_2$SiO)$_{15}$(MeZSiO)SiMe$_3$)]$^+$$_2$Cl$^-$$_2$ where Z is (CH$_2$)$_3$N(CH$_3$)CH$_2$CH$_2$N(CH$_3$)$_2$ was prepared in the following way. An N-(N',N'-dimethylaminoethyl)-N-methylaminopropyl-functional polysiloxane was prepared according to the scheme (Me$_3$SiO)$_2$MeSi(CH$_2$)$_3$N(CH$_3$)CH$_2$CH$_2$N(CH$_3$)$_2$ +

Me$_3$SiO(Me$_2$SiO)$_{15}$(MeSi(CH$_2$)$_3$N(CH$_3$)CH$_2$CH$_2$N(CH$_3$)$_2$)OSiMe$_3$. 3.65 g of (Me$_3$SiO)$_2$MeSi(CH$_2$)$_3$N(CH$_3$)CH$_2$CH$_2$N(CH$_3$)$_2$, 11.0 g (Me$_2$SiO)$_n$ and 5 ml tetrahydrofuran with 0.3 g KOH and 0.3 g H$_2$O were heated to 80° C. for 10 hours. After cooling to room temperature, the mixture was diluted with 50 ml petroleum ether, washed four times with water, and dried with MgSO$_4$. The petroleum liquid was distilled off at room temperature in vacuum and the remaining liquid was stripped at 0.3 mbar/150° C. 3.2 g distillate were taken off. 10.2 g viscous pale yellow liquid remained in the flask.

0.2 g Cu$_2$Cl$_2$ was suspended in 5 ml methanol and 3.1 g of 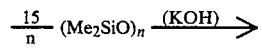 Me$_3$SiO(Me$_2$SiO)$_{15}$(MeSi(CH$_2$)$_3$N(CH$_3$)CH$_2$CH$_2$N(CH$_3$)$_2$)OSiMe$_3$ was added to the stirred mixture in an open flask. The colour of the mixture (two phases) changed to deep blue. The mixture was stirred for 18 hours and then all volatile compounds were removed at room temperature under vacuum. The remaining green oil was dissolved in 10ml toluene and filtered through diatomaceous silica to remove unreacted Cu$_2$Cl$_2$. From the filtrate, the toluene was distilled off in vacuum (0.3 mbar/40° C.). The remaining green viscous oil partially solidified. It was soluble in toluene, acetone and slightly soluble in polydimethylsiloxane fluid.

A third illustrative complex was prepared according to the scheme $Cu_2Cl_2 + 2L + H_2O + \frac{1}{2}O_2 \rightarrow (Cu(OH)L)_2Cl_2$ in which L represents $(Me_3SiO)_2MeSi(CH_2)_3NHCH_2CH_2NH_2$. 3.2 g $Cu_2Cl_2$ was suspended in 15 ml methanol, 0.2 ml water was added and then 6.4 g L. This mixture was stirred in air for 5 hours. Within the first minutes an exothermic reaction started and the colour of the reaction mixture changed from pale green to intensive blue. All volatile components were then distilled off under vacuum at room temperature and the blue green solid residue was dissolved in toluene and filtered through diatomaceous earth. The solvent was removed again and a blue green solid remained.

EXAMPLE 1

In this Example, a first arylolsilicon compound was employed. This compound was made in the following way. 9.1 g 2-allyl-6-methylphenol were dissolved in 100 ml toluene, $(7.7 \times 10^{-6}$ mol$)$ chloroplatinic acid added and heated under stirring to 85°–90° C. Within 20 minutes 90.0 g $Me_3SiO(Me_2SiO)_{95}(MeHSiO)_5SiMe_3$ were added and the temperature kept at 90° C. for 2 hours. In vacuum, the toluene and all other volatile compounds were distilled off (up to 0.2 mbar/140° C.).

A yellow viscous oil remained in the flask, this material being according to the general formula $Me_3SiO(Me_2SiO)_{95}(MeSiO)_5SiMe_3$

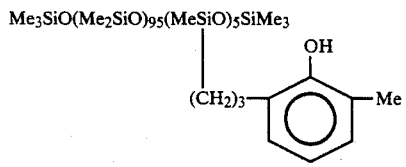

68.3 mg of the first illustrative complex was dissolved in 0.5 ml toluene and then added to 7.11 g of the first arylolsilicon compound to provide a formulation in the form of a solution containing about 1% by weight complex. This mixture was kept under nitrogen at room temperature. The solution had a pale yellow-green colour which turned after three days to a colloidal red, which did not change for the next four weeks. A sample brought into contact with air had a skin over-time of less than one minute and was tackfree within half an hour. A sample in a 5 mm glass tube open to the air cured within 3 months to a depth of about 20 mm. During curing the colloidal red colour disappeared leaving a clear yellow-green solution and then became brown as the curing progressed. The above red colloidal solution was stirred in contact with air for a few minutes, whereupon the red colour disappeared and the whole solution became clear again. Air was removed from the flask again by evacuating and filling with nitrogen. The solution remained liquid, no colour change or crosslinking could be observed. During further storage, the colour changed again to red. The formulation was thus stable in air-free storage but cured in presence of air.

EXAMPLE 2

In this example, 15 g of the first arylolsilicon compound was employed, together with 150 mg (1 wt %) of the second illustrative complex. These materials were mixed under nitrogen to provide a formulation in the form of a pale yellow solution, degassed and poured into sample tubes open to the air. After 2 minutes, a skin had been formed and the mass has tack-free within 20 minutes. The cured siloxane had a brown colour which served as an indication of the depth to which curing had extended into the mass namely after 24 hours 3.5 mm; after 3 days 4.5 mm; after 11 days 6 mm; after 4 weeks 10 mm. After about one week from mixing, a red colloidal precipitate appeared in the uncured part, divided from the cured part by a 0.5–1.0mm thick zone of clear pale yellow material.

A second mixture was set up with 0.1% of the same complex. Within three hours no skin was formed but the siloxane changed colour from pale yellow to light brown to a depth of 15 mm. 24 hours after exposure to air the surface was tack-free. After 4 weeks it had cured to a depth of 20 mm. The uncured siloxane remained a clear, pale yellow.

EXAMPLE 3

In this example the second illustrative complex was employed together with a second arylolsilicon compound prepared in the following way.

9.4 ml eugenol was dissolved in 100 ml toluene, $7.7 \times 10^{-6}$ mol chloroplatinic acid added and the mixture heated under stirring to 90° C. 90.0 g $Me_3SiO(Me_2SiO)_{95}(MeHSiO)_5SiMe_3$ was added within 30 minutes. The temperature was kept at 90° C. for 2.5 hours. The toluene and all other volatile compounds were stripped off (at 0.2 mbar/140° C.). A yellow viscous oil remained, this material being according to the general formula

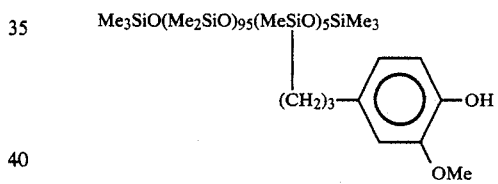

This compound differs from the first arylolsilicon compound in the identity and location of substituents of the phenyl ring. A formulation consisting of a mixture of the second arylolsilicon compound and 0.5% by weight of the second illustrative complex changed colour after exposure to air. Within one hour, the colour of the surface of the liquid changed from pale yellow to red-brown. After 24 hours it was still liquid, a skin was produced only after 3 days but the surface was still tacky and the colour of the total sample throughout the total depth of 40 mm had changed to red-brown. After 11 days it was tack-free and the colour was slightly darker.

EXAMPLE 4

In this example, a third arylolsilicon compound was used. This compound differed from the first arylolsilicon compound in the number of reactive sites i.e. phenol groups available in each polysiloxane chain. The third arylolsilicon compound was prepared in the following way.

-continued

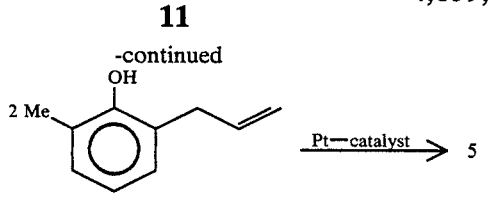

56.2 g Me$_2$HSiO(Me$_2$SiO)$_{150}$SiMe$_2$H, 1.5 g 2-allyl-6-methylphenol, 50 ml toluene and $3.1 \times 10^{-6}$ mol chloroplatinic acid mixed and heated under stirring to 85°–90° C. for 2.5 hours. The product was stripped from toluene and other volatile compounds at 0.3 mbar/160° C. The material produced was according to the general formula

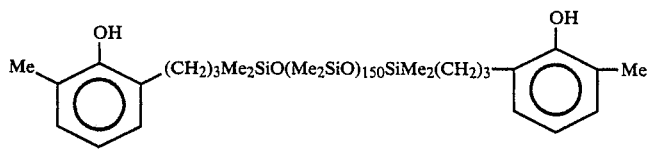

A formulation consisting of a mixture of this third arylolsilicon compound and 0.5% by weight of the second illustrative complex had a brown surface after exposure to air for 20 seconds. A skin formed slowly, after several hours, and the surface was tack-free after 24 hours.

In-depth curing of the sample was observed to proceed slowly, thus after 24 hours 5 mm; after 2 days 6.5 mm; after 11 days 10 mm and after 4 weeks 17 mm. A small amount of a colloidal precipitate appeared in the uncured siloxane.

EXAMPLE 5

0.15 g of the third illustrative complex as a solution in 0.5 ml toluene was blended with 9 g of the third arylolsilicon compound to provide a formulation in the form of a green viscous solution. This solution was poured into a shallow dish and exposed to air at room temperature. After 3 hours the solution had thickened at the surface and after 16 hours the surface was rubbery and tack free. Within 2 days the sample was cured fully through to a depth of 4 mm.

EXAMPLE 6

In this example the first illustrative complex was employed together with a first a phenylcyanoacetylsiloxane. The siloxane was prepared as follows. 55 g of carbohydroxy functional siloxane represented thus

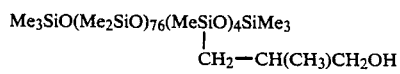

and 5.6 g of methyl-phenylcyanoacetate was heated under vacuum (3 mbar) to 180° C. whereupon methanol distilled off from the reaction mixture. The obtained product was according to the average general formula 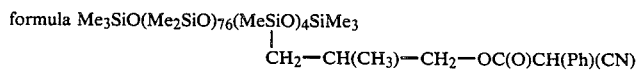

which was a viscous pale yellow liquid, 100 parts of this phenylcyanoacetoxy-functional siloxane and 1 part of the first illustrative complex were blended under nitrogen and then exposed to air at room temperature. Within 1 hour a skin had been formed on the surface of the sample, after 24 hours the sample was cured to a depth of 5 mm and after 4 months to 27 mm. Contrary to this result, a sample of this phenylcyanoacetoxy-functional siloxane without any additives was exposed to air under identical conditions but was still liquid after one day.

EXAMPLE 7

In this example, the first illustrative complex was employed together with a second phenylcyanoacetylsiloxane. The siloxane was prepared as follows. 7.8 g of aminopropyl-functional siloxane represented thus

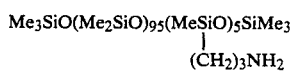

and 0.88 g of methyl-phenylcyanoacetate was heated under vacuum (3 mbar) to 90°–100° C. whereupon methanol distilled off from the reaction mixture. After 20 minutes, the obtained product was according to the average general formula

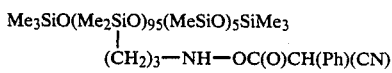

which was a very viscous pale yellow liquid. 100 parts of this phenylcyanoacetoxy-functional siloxane and 1 part of the first illustrative complex were blended under nitrogen, degassed under vacuum and then exposed to air at room temperature. Within 30 minutes, a skin had been formed on the surface of the sample and after 20 hours, the sample, was cured to a clear pale green tack-free rubber to a depth of 5 mm.

EXAMPLE 8

In this example, the first illustrative complex was employed together with a third phenylcyanoacetylsiloxane. The siloxane was prepared as follows. 93 g of aminopropyl functional siloxane represented thus

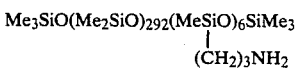

and 4.2 g of methyl-phenylcyanoacetate was heated under vacuum (3 mbar) to 115° C. whereupon methanol distilled off from the reaction mixture. The obtained product was according to the average general formula

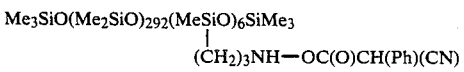

100 parts of this phenylcyanoacetoxy-functional siloxane and 0.8 part of the first illustrative complex were blended under nitrogen, degassed under vacuum and then exposed to air at room temperature. Within 5 hours, a skin had been formed on the surface of the sample, and after 24 hours the surface was tack-free and the sample cured to a depth of 6 mm. After 2 weeks, the sample had cured to a depth of 20 mm.

That which is claimed is:

1. A composition comprising a complex of a copper salt in oxidation state II formed by mixing in the presence of oxygen, water, copper or a copper salt, and an organosilicon compound comprising at least one unit according to the general formula (i)

$$O_{\frac{3-a}{2}} SiR_aR'$$

in which each R represents a monovalent group attached to the silicon atom and each R, represents a group including two amino nitrogen atoms linked by a group R'' having a structure such that the two nitrogen atoms enter into a heterocyclic ring structure of two nitrogen atoms, a copper atom, and from 2 to 5 inclusive carbon atoms linking the nitrogen atoms, and a is an integer with a value of less than 4.

2. A composition according to claim 1 wherein the organosiloxane compound is an organosiloxane comprising at least one unit of the general formula (i) and at least one unit according to the general formula (ii)

$$O_{\frac{4-b}{2}} SiR_b$$

in which each R represents a monovalent group attached to the silicon atom and b is an integer with a value of less than 4.

3. A composition according to claim 1 wherein the group R, is characterized by the general formula (iii) $R^3N(Q)R''NQ_2$ in which $R^3$ represents an alkylene group having a chain of at least three carbon atoms linking silicon and nitrogen atoms, R'' represents an alkylene group having from 2 to 5 inclusive carbon atoms linking the nitrogen atoms and each Q is selected from the group consisting of a hydrogen atom and an alkyl group attached to a nitrogen atom.

4. A composition according to claim 3 wherein each Q is selected from the group consisting of a hydrogen atom, a methyl group and an ethyl group.

5. A composition according to claim 3 wherein $R^3$ represents a propylene group and R'' is selected from the group consisting of an ethylene and a propylene group.

6. A composition according to claim 2 wherein the organosiloxane includes from 5 to 30 units according to the general formula (ii) and a has a value chosen from 1 and 2.

7. The composition according to claim 1 wherein said composition further comprises a silicon compound curable by a oxidation coupling reaction in the amounts of 100 parts by weight of the silicon compound for up to 5 parts by weight of the complex.

8. The composition according to claim 7 in which the R' group has the general formula (iii)

$$R^3N(Q)R''NQ_2$$

in which $R^3$ represents an alkylene group having a chain of at least three carbon atoms linking silicon and nitrogen atoms, R'' represents an alkylene group having from 2 to 5 inclusive carbon atoms linking the nitrogen atoms and each Q is selected from the group consisting of a hydrogen atom and an alkyl group attached to a nitrogen atom.

9. The composition according to claim 8 in which each Q is selected from the group consisting of hydrogen atom, methyl group, and ethyl group.

10. The composition according to claim 8 in which $R^3$ represents a propylene group and R'' is selected from the group consisting of ethylene and propylene.

11. A composition according to claim 7 wherein the organosilicon compound is an organosiloxane comprising at least one unit of the general formula (i) and at least one unit according to the generally formula (ii)

$$O_{\frac{4-b}{2}} SiR_b$$

in which each R represents a monovalent group attached to the silicon atom and b is an integer with a value of less than 4.

12. The composition according to claim 11 in which the organosiloxane includes from 5 to 30 units according to the general formula (ii) and a has a value chosen from 1 and 2.

13. The composition according to claim 11 in which the organosiloxane has the average general formula $$R_3Si(OSiR_2)_x(OSiR_3-\overset{R}{\underset{|}{N}}-R''-\overset{Q}{\underset{|}{N}}Q_2)_yOSiR_3$$

in which x has a value from 12 to 20, y has a value from 1 to 3 and at least 85% of the R groups present are methyl.

14. A composition according to claim 7 in which the silicon compound is an arylolsilicon compound comprising units according to the general formula (iv)

$$O_{\frac{4-b}{2}} SiA_b$$

and at least one unit according to the general formula (v)

$$O_{\frac{3-c}{2}} Si(A)_c(A'A''OH)$$

in which each A is selected from the group consisting of a monovalent hydrocarbon group, a halogenated monovalent hydrocarbon group, a cyanoalkyl group, and an unsaturated hydrocarbon group attached to a silicon atom, each A, is selected from the group consisting of a substituted and an unsubstituted divalent group, and A'' is selected from the group consisting of phenylene and a substituted phenylene group, b and c are integers having a value of from 0 to 3.

15. The composition according to claim 14 wherein the arylolsilicon compound comprises from about 2 to about 10 units according to the general formula (v) per molecule.

16. The composition according to claim 14 wherein each A represents methyl, each A' represents —(CH$_2$)$_3$—, b has a value chosen from 2 and 3, and c has a value chosen from 1 and 2.

17. The composition according to claim 14 wherein each A" is selected from the group consisting of

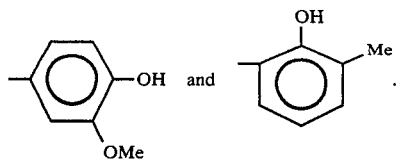

18. The composition according to claim 7 wherein the silicon compound is an arylcyanoacetylsilicon compound comprising units according to the general formula (iv)

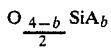

and at least one according to the general formula (vi)

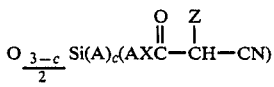

in which each a is selected from the group consisting of a monovalent hydrocarbon group, a halogenated monovalent hydrocarbon group, a cyanoalkyl group, and an unsaturated hydrocarbon group attached to a silicon atom, each A, is selected from the group consisting of a substituted and an unsaturated divalent group, X is selected from the group consisting of an oxygen atom and the group =NH, Z is selected from the group consisting of phenyl and a substituted phenyl group, and b and c have a value from 0 to 3.

19. The composition according to claim 18 wherein the arylcyanoacetylsilicon compound comprises from about 2 to about 10 units according to the general formula (vi) per molecule.

20. The composition according to claim 18 wherein each A represents methyl, each A is chosen from the group consisting of —(CH$_2$)$_3$— and —CH$_2$—CH(CH$_3$CH$_2$—, b has a value chosen from 2 and 3, and c has a value chosen from 1 and 2.

21. A composition according to claim 2 wherein the organosiloxane has the average general formula R$_3$Si(OSiR$_2$)$_x$(OSi(R)R$^3$N(Q)R"NQ$_2$)$_y$OSiR$_3$ in which x has a value from 12 to 20, y has a value from 1 to 3 and at least 85% of the R groups present are methyl groups and R$^3$ represents an alkylene group having a chain of at least three carbon atoms linking silicon and nitrogen atoms.

22. A formulation comprising 100 parts by weight of a silicon compound curable by an oxidative coupling reaction, said formulations being selected from the group consisting of arylolsilicones and arylcyanoacetylsilicones, and up to 5 parts by weight of a catalyst for said reaction which is a composition comprising a complex of a copper salt in oxidation state II formed from copper or a copper salt, an organosilicon compound including at least one unit according to the general formula (i)

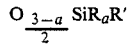

in which each R represents a monovalent group attached to the silicon atom, R, represents a group including two amino nitrogen atoms linked by a group R" having a structure such that the two nitrogen atoms may enter into a heterocyclic ring structure including two nitrogen atoms, a copper atom and from 2 to 5 inclusive carbon atoms linking the nitrogen atoms and a is an integer with a value of less than 4 and water in presence of oxygen.

* * * * *